(12) United States Patent
Kim et al.

(10) Patent No.: US 8,426,383 B2
(45) Date of Patent: Apr. 23, 2013

(54) **ANTI-AGING COMPOSITION FOR EXTERNAL USE COMPRISING LOW AND HIGH MOLECULAR WEIGHT HYALURONIC ACIDS AND THE POLYSACCHARIDES EXTRACTED FROM ROOT BARK OF *ULMUS DAVIDIANA***

(75) Inventors: Ki Ho Kim, Cheonan-si (KR); Ki Soo Kim, Cheongju-si (KR); Young Heui Kim, Cheonan-si (KR); Jin Guk Kim, Cheonan-si (KR); Kyoung Tae Kim, Asan-si (KR); Chang Sung Han, Cheonan-si (KR); Kang Il Ko, Seoul (KR)

(73) Assignee: Bioland Ltd. (KR)

( * ) Notice: Subject to any disclaimer, the term of this patent is extended or adjusted under 35 U.S.C. 154(b) by 279 days.

(21) Appl. No.: 12/922,353

(22) PCT Filed: Mar. 12, 2009

(86) PCT No.: PCT/KR2009/001246
§ 371 (c)(1),
(2), (4) Date: Sep. 13, 2010

(87) PCT Pub. No.: WO2009/113820
PCT Pub. Date: Sep. 17, 2009

(65) Prior Publication Data
US 2011/0003769 A1 Jan. 6, 2011

(30) Foreign Application Priority Data
Mar. 13, 2008 (KR) ........................ 10-2008-0023260

(51) Int. Cl.
*A61K 8/73* (2006.01)
*A61K 31/728* (2006.01)
*A61P 17/00* (2006.01)
*A61Q 19/08* (2006.01)
*A61Q 19/00* (2006.01)

(52) U.S. Cl.
USPC ............................................ 514/54

(58) Field of Classification Search .............. 514/54
See application file for complete search history.

(56) References Cited

U.S. PATENT DOCUMENTS
5,340,579 A * 8/1994 Casero ..................... 424/114
6,689,349 B1 * 2/2004 Wohlrab et al. ........... 424/78.02

FOREIGN PATENT DOCUMENTS
KR  89-003708  9/1989
KR  10-2003-0061759  7/2003
KR  10-2007-0000057  1/2007

OTHER PUBLICATIONS

Eom et al, J. Cosmetic Sci., 2006, 57, 355-67.*
Kyung-Soo Nam et al., "Effect of Water Extract from *Thesium chinese* Tunczaninov and *Prunella vulgaris* L. on Aromatase and Cyclooxygenase Activities," Kor. J. Pharmacogn, vol. 35, No. 2, 2004, pp. 147-151.
Laura C. Green et al., "Analysis of Nitrate, Nitrite, and [15N] Nitrate in Biological Fluids," Analytical Biochemistry, vol. 126, 1982, pp. 131-138.

* cited by examiner

Primary Examiner — Shaojia Anna Jiang
Assistant Examiner — Ganapathy Krishnan
(74) Attorney, Agent, or Firm — Cantor Colburn LLP

(57) ABSTRACT

Disclosed is an anti-aging composition for external use on skin, which includes low-molecular weight hyaluronic acids, high-molecular weight hyaluronic acids and polysaccharides extracted from root bark of *Ulmus davidiana*, as active ingredients. The composition including the low-molecular weight hyaluronic acids, high-molecular weight hyaluronic acids and polysaccharides extracted from root bark of *Ulmus davidiana*, in a predetermined ratio, shows significantly improved skin-moisturizing, skin elasticity-enhancing and inflammation-alleviating effects, as compared to a composition using one of the above ingredients alone. Therefore, the composition may be widely used as a pharmaceutical or cosmetic anti-aging composition.

4 Claims, No Drawings

ANTI-AGING COMPOSITION FOR EXTERNAL USE COMPRISING LOW AND HIGH MOLECULAR WEIGHT HYALURONIC ACIDS AND THE POLYSACCHARIDES EXTRACTED FROM ROOT BARK OF ULMUS DAVIDIANA

TECHNICAL FIELD

The present invention relates to an anti-aging composition including low-molecular weight hyaluronic acids, high-molecular weight hyaluronic acids and polysaccharides extracted from root bark of *Ulmus davidiana*. More particularly, the present invention relates to a pharmaceutical or cosmetic anti-aging composition for external use on skin, which includes low-molecular weight hyaluronic acids, high-molecular weight hyaluronic acids and polysaccharides extracted from root bark of *Ulmus davidiana*.

BACKGROUND ART

Aging is a phenomenon that appears as living organisms grow older and includes degradation in physiological functions of living bodies caused by a change in cells, genes or proteins. Skin aging begins gradually at an age of 17-25, when body growth is terminated. Even after skin aging begins, the epidermis is changed (regenerated) through the division of basal cells. However, the dermis does not grow any longer. Main factors causing such phenomena include loss of moisture in the skin accompanied by degradation in biosynthesis of intercellular substances resulting from intracellular inflammation. Therefore, in order to reduce wrinkles and prevent aging, it is required to maintain the skin in a moisturized state, to protect the skin from the external environment, and to inhibit inflammation in the skin.

Among several layers forming the skin, the epidermis is the most important layer that protects the body from the external environment and maintains the skin in an elastic and moisturized state. The epidermis functions to inhibit foreign materials from penetrating into the living body and to prevent loss of moisture inside the living body. Maintenance of an adequate amount of moisture is very important to maintain the skin elasticity and softness. Meanwhile, as skin aging proceeds, reduced secretion of sebum results in a lack of skin oil and degradation of the capability of preventing skin moisture evaporation, thereby causing drying of the epidermis and generation of fine wrinkles. In addition, when external irritation factors, such as sunlight, are applied continuously to the skin, keratinocytes generate various chemicals, such as cytokines, and the information thereof is transferred to the cells in the dermis, resulting in a change in the metabolism of fibroblasts. Further, when cytokines act on vascular endothelial cells, immune cells including lymphocytes secrete enzymes, such as collagenase or elastase, which decompose fibrous proteins, in blood vessels, thereby causing decomposition of collagen and elastin. As a result, there is generated an imbalance between the amount of newly synthesized fibrous proteins and the amount of decomposed fibrous proteins. When the process is repeated, skin elasticity is lowered and wrinkles or skin sagging phenomena occur. In addition to the above, as the human body undergoes aging, immune functions are lowered and the skin becomes dry and rough, so that the skin is susceptible to infection by bacteria and may suffer from a serious inflammation. Further, as the skin cornification cycle become longer, the horny layer grows thicker and rougher.

Inflammation is caused by the activation of inflammatory factors due to the oxidative stresses including ultraviolet rays (UV), reactive oxygen species, free radicals, etc., and results in various diseases and skin aging. One of the characteristics of inflammation is an increased in addition of oxygen to arachidonic acid metabolized via the cyclooxygenase (COX) pathway, by which prostaglandin is produced, and the 5-lipoxygenase pathway, by which leukotriene is produced. Both prostaglandin and leukotriene are mediators of inflammation. Therefore, therapeutic methods designed to inhibit activities of COX and/or lipoxygenase have been recently spotlighted. COXs are classified into two types: COX-1 and COX-2. It seems that the latter, i.e., COX-2, plays an important role in the progress of inflammation. Additionally, unlike the irreversible inhibition of COX-1, inhibition of COX-2 is effective for reducing inflammation without any related side effects.

Another strong inflammation mediator is nitric oxide (NO), which is produced from L-arginine by NO synthase (NOS), and is generated in many types of cells due to stresses, such as UV, endotoxin, cytokines, etc. Such inflammatory stimuli increase the expression of inducible NOS in cells to generate NO, and activate macrophages to cause inflammation.

Hyaluronic acids used herein are found in the placenta, eyes and joints of animals, the cockscomb, etc., and have been commercialized in the fields of medicines, cosmetics and foods. More recently, hyaluronic acids have been produced and used via a fermentation process using microorganisms, considering the possibility of infective diseases that may be derived from animals. Hyaluronic acids have a chain structure in which D-glucuronic acid and N-acetyl-D-glucosamine are linked via $\beta$-1,3 bonding repeatedly, wherein the repeating units are linked with each other via $\beta$-1,4 bonding. Hyaluronic acids are molecular clusters whose molecular weights range from hundreds of thousands to several millions of Daltons (Da), and have very high viscosity. Hyaluronic acids function to allow cells to be in contact with each other, to soften joints, or to bind or support the whole body, skin, organs or cells. Hyaluronic acids are found in substantially all parts of the human body, particularly in the subcutaneous fat layer, joint portions, synovial fluid, umbilical cords and the lenses of eye balls at a high amount. It is reported that hyaluronic acids participate in maintaining intercellular distances, cell division and differentiation, transfer, immune modulation, etc. It is also reported that the amount of hyaluronic acids in the human skin decreases as the aging proceeds. It is thought that such a decrease in hyaluronic acids is one of the direct causes of degradation of skin elasticity and a drop in moisture content. The inventors recently found that hyaluronic acids show different in vivo mechanisms and effects depending on their molecular weights. In brief, high-molecular weight hyaluronic acid functions to inhibit loss of skin moisture by forming a film on the skin. On the other hand, low-molecular weight hyaluronic acid penetrates into the cell layer, which is hardly penetrated by high-molecular weight hyaluronic acid, as much as 16.0%, as measured by the cell layer penetration test using Caco-2 cells. Additionally, low-molecular weight hyaluronic acid shows a permeability as high as about 90% in the skin permeation test using artificial skin. Further, through measurement of the skin moisture content and transdermal moisture loss, low-molecular weight hyaluronic acid is confirmed to have a high moisturizing effect comparable to that of high-molecular weight hyaluronic acid.

*Ulmus davidiana* is a deciduous broad-leaved tree belonging to the family Ulmaceae, the order Urticales, of the division Dicotyledon, and is also called spring elm or house elm. *Ulmus davidiana* is a deciduous arbor as tall as about 10 m. The leaves have a broad ellipsoidal shape and teeth. In spring, light green-colored small flowers blossom in a group. *Ulmus davidiana* is also called elm (榆), and the bark thereof is called elm bark (榆皮) or white elm bark (榆白皮) and the root bark thereof is called elm root bark (榆根皮) in Chinese character. The bark contains flavonoids, saponins, tannins (3%) and a large amount of viscous materials. The root bark of *Ulmus davidiana* is used after the root bark is peeled around June and the outer shell is trimmed before drying under the sunlight. The extract of root bark from *Ulmus davidiana* is reported to have the effect of alleviating inflammation. In addition, the extract of *Ulmus davidiana* reinforces motions of the small intestine and the smooth muscle of bladder, and has cough-alleviating, astringenting and anti-inflammatory effects. In folk remedies, elm bark is boiled down so that it is taken for treating stomachaches or backaches. The other applications include an anti-inflammatory salve to be applied to festering wounds.

DISCLOSURE

Technical Problem

The anti-aging composition disclosed herein is a result of consistent studies to solve the problems occurring in the related art when low-molecular weight hyaluronic acid, high-molecular weight hyaluronic acid or extract of root bark of *Ulmus davidiana* is used alone. The anti-aging composition disclosed herein includes: low-molecular weight hyaluronic acid that has excellent skin permeability and shows moisturizing and hyaluronic acid synthesis-accelerating effects in the skin; high-molecular weight hyaluronic acid that forms a moisturizing film on the outer surface of the skin; and extract of root bark of *Ulmus davidiana* having an excellent anti-inflammatory effect.

Technical Solution

Disclosed is an anti-aging composition including: low-molecular weight hyaluronic acid that has excellent skin permeability and shows moisturizing and hyaluronic acid synthesis-accelerating effects in the skin; high-molecular weight hyaluronic acid that forms a moisturizing film on the outer surface of the skin; and extract of root bark of *Ulmus davidiana* having an excellent anti-inflammatory effect.

Disclosed also is a pharmaceutical or cosmetic anti-aging composition that uses the above composition and shows significantly improved skin-moisturizing, skin elasticity-enhancing and inflammation-alleviating effects, as compared to a composition using one of the above ingredients alone.

Advantageous Effects

The anti-aging composition disclosed herein shows significantly improved skin-moisturizing, skin elasticity-enhancing and inflammation-alleviating effects, as compared to a composition using one of the above ingredients alone.

BEST MODE

Exemplary embodiments now will be described more fully hereinafter with reference to the accompanying drawings, in which exemplary embodiments are shown. The present invention may, however, be embodied in many different forms and should not be construed as limited to the exemplary embodiments set forth therein. Rather, these exemplary embodiments are provided so that this disclosure will be thorough and complete, and will fully convey the scope of the present invention to those skilled in the art. In the description, details of well-known features and techniques may be omitted to avoid unnecessarily obscuring the presented embodiments.

The terminology used herein is for the purpose of describing particular embodiments only and is not intended to be limiting of the present invention. Unless otherwise defined, all terms (including technical and scientific terms) used herein have the same meaning as commonly understood by one of ordinary skill in the art. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

In one aspect, there is provided a pharmaceutical anti-aging composition for external use on skin, which includes, as active ingredients, high-molecular weight hyaluronic acids, low-molecular weight hyaluronic acids and polysaccharides extracted from root bark of *Ulmus davidiana*. Hyaluronic acids used in the anti-aging composition disclosed herein are represented by the following Formula 1:

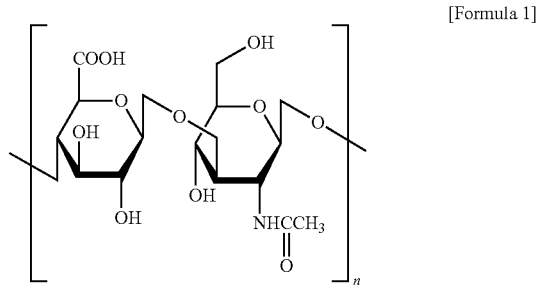

[Formula 1]

After providing the composition including low-molecular weight hyaluronic acids, high-molecular weight hyaluronic acids and polysaccharides separated from root bark of *Ulmus davidiana*, the skin-moisturizing, skin elasticity-enhancing and inflammation-alleviating effects of the composition were tested. As a result, it was shown that a combination of low-molecular weight hyaluronic acids, high-molecular weight hyaluronic acids and polysaccharides separated from root bark of *Ulmus davidiana* at a predetermined ratio has an unexpectedly markedly improved anti-aging effect as compared to a composition including low-molecular weight hyaluronic acids, high-molecular weight hyaluronic acids or polysaccharides separated from root bark of *Ulmus davidiana* alone.

The high-molecular weight hyaluronic acids used in the composition disclosed herein may be prepared via fermentation using microorganisms or extraction from animal organs. More specifically, the high-molecular weight hyaluronic acids may be produced by culturing *Streptococcus* bacteria, such as *Streptococcus equi, Streptococcus zooepidemicus*, etc. Additionally, the low-molecular weight hyaluronic acids used in the composition disclosed herein may be produced by hydrolyzing the high-molecular weight hyaluronic acid under an acidic condition by a known method. More particularly, the high-molecular weight hyaluronic acids used herein were obtained by inoculating *Streptococcus equi* (KCTC 1873) into a culture medium, culturing it for 24 hours, and carrying out purification via precipitation in alcohol, according to the method described in Korean Patent Publication No. 1989-0003708. The high-molecular weight hyaluronic acids have an average molecular weight of 500,000-3,000,000 Da. Then, the low-molecular weight hyaluronic acids used herein were obtained by treating the high-molecular weight hyaluronic acid in a strong acidic ion exchange resin, followed by precipitation in alcohol, according to the method described in Korean Patent Registration No. 10-0665916-0000. The low-molecular weight hyaluronic acids are determined to have a molecular weight of 500-50,000 Da.

The polysaccharides from root bark of *Ulmus davidiana* used in the composition disclosed herein are obtained by completely drying root bark of *Ulmus davidiana*, and extracting the dried root bark of *Ulmus davidiana* with any extraction process known to those skilled in the art. The extraction may be carried out by using any known solvents such as water, phosphate buffers, weakly basic aqueous solutions, glycerin, ethylene glycol and propylene glycol. More particularly, the polysaccharides used herein were extracted from root bark of *Ulmus davidiana var. japonica* according to the method described in Korean Patent Registration No. 10-0445430-0000. First, root bark of *Ulmus davidiana var. japonica* is dried completely and an extraction solvent is added thereto in an amount corresponding to 5-30 times the volume of the dry weight of root bark of *Ulmus davidiana var. japonica*. The extraction solvent may be at least one solvent selected from the group consisting of water, phosphate buffers, weakly basic aqueous solutions, glycerin, ethylene glycol and propylene glycol. Next, active ingredients are extracted by heating the mixture in an extraction device equipped with a cooling condenser to prevent solvent evaporation at 30-70° C. for 4-48 hours, or by dipping the dried root bark of *Ulmus davidiana var. japonica* in the extraction solvent at 5-37° C. for 1-15 days. Then, the extracted active ingredients are subjected to precipitation in at least one solvent selected from the group consisting of methanol, ethanol, propanol, butanol and acetone. The polysaccharides obtained as described above have a molecular weight (Mw) of 10,000-35,000 and an intrinsic viscosity of 80-100 dL/g.

In the pharmaceutical anti-aging composition disclosed herein, the high-molecular weight hyaluronic acids may have an average molecular weight of 500,000-3,000,000 Da, while the low-molecular weight hyaluronic acids may have an average molecular weight of 500-50,000 Da, more specifically 500-10,000 Da. In practice, molecular weights of hyaluronic acids in natural biological substances vary a lot. Molecular weights of hyaluronic acids may depend on the particular analyzing techniques or techniques for separation from the sources of hyaluronic acids.

The pharmaceutical anti-aging composition disclosed herein may include the low-molecular weight hyaluronic acids in an amount of 0.1-80 wt %, the high-molecular weight hyaluronic acids in an amount of 0.1-70 wt % and the polysaccharides extracted from root bark of *Ulmus davidiana* in an amount of 0.1-70 wt %, based on the total weight of the composition. More particularly, the pharmaceutical anti-aging composition disclosed herein may include the low-molecular weight hyaluronic acids in an amount of 15-70 wt %, the high-molecular weight hyaluronic acids in an amount of 15-60 wt % and the polysaccharides extracted from root bark of *Ulmus davidiana* in an amount of 15-60 wt %, based on the total weight of the composition. In Example 1, compositions of the hyaluronic acids and polysaccharides extracted from root bark of *Ulmus davidiana* are prepared in the above-specified range (see Table 1).

The pharmaceutical anti-aging composition disclosed herein has a moisturizing effect. In Test Example 1 of Example 1, a moisturizing effect tester (Corneometer CM825) was used to measure the moisturizing effect. After the test, it is observed that the composition including the low-molecular weight hyaluronic acids, high-molecular weight hyaluronic acids and polysaccharides extracted from root bark of *Ulmus davidiana* as active ingredients shows an unexpectedly markedly improved moisturizing effect, as compared to a composition including low-molecular weight hyaluronic acids, high-molecular weight hyaluronic acids or polysaccharides extracted from root bark of *Ulmus davidiana* alone (see Table 2).

The pharmaceutical anti-aging composition disclosed herein has a skin elasticity-enhancing effect. In Test Example 2 of Example 1, an elasticity tester (Cutometer MPA580) was used to measure the skin elasticity-enhancing effect. After the test, it is observed that the composition including the low-molecular weight hyaluronic acids, high-molecular weight hyaluronic acids and polysaccharides extracted from root bark of *Ulmus davidiana* active ingredients shows an unexpectedly markedly improved skin elasticity-enhancing effect, as compared to a composition including low-molecular weight hyaluronic acids, high-molecular weight hyaluronic acids or polysaccharides extracted from root bark of *Ulmus davidiana* alone (see Table 3).

The pharmaceutical anti-aging composition disclosed herein has an anti-inflammatory effect. In an inflammation response, prostaglandin and leukotriene act as inflammation mediators. Thus, inhibition of cyclooxygenase (COX)-2 producing prostaglandin may reduce inflammation without any related side effects, unlike the irreversible inhibition of COX-1 (see, Kyung-Soo Nam, et al, *Kor. J. Pharmacogn.*, 35(2), pp-147-151, 2004). Another strong inflammation mediator, nitric oxide (NO), is produced from L-arginine by NO synthase (NOS) and is generated in many types of cells by stresses, such as UV, endotoxin or cytokines. Such inflammatory stimuli increase expression of intracellular inducible NOS to generate NO, and activate macrophages to cause inflammation. In Test Example 3 of Example 1, reverse transcription-polymerase chain reaction of COX-2 with NOS genes was performed to measure the inflammation-inhibiting effect. After the test, it is observed that the composition including the low-molecular weight hyaluronic acids, high-molecular weight hyaluronic acids and polysaccharides extracted from root bark of *Ulmus davidiana* as active ingredients shows an unexpectedly markedly improved inflammation-inhibiting effect, as compared to a composition including low-molecular weight hyaluronic acids, high-molecular weight hyaluronic acids or polysaccharides extracted from root bark of *Ulmus davidiana* alone (see Table 5).

The pharmaceutical anti-aging composition disclosed herein is shown to have anti-aging activities in itself. Therefore, the anti-aging composition may be formed into any formulations applied onto the skin or hair. More particularly, such formulations may include creams, gels, patches, spray agents, ointments, plasters, lotions, liniments, pastes and cataplasms. Since the pharmaceutical anti-aging composition disclosed herein is for external use, there is no possibility that the composition is absorbed into the human body to cause side effects. Additionally, the pharmaceutical anti-aging composition causes no skin irritation. The low-molecular weight hyaluronic acids, high-molecular weight hyaluronic acids and polysaccharides extracted from root bark of *Ulmus davidiana* may be used in any suitable ratios, as long as they are combined homogeneously with pharmaceutically acceptable additives. In the following Preparation Examples, skin softener, nourishing lotion, nourishing cream and hydrophilic ointment, each containing 10 wt % of the composition of the low-molecular weight hyaluronic acids, high-molecular weight hyaluronic acids and polysaccharides extracted from root bark of *Ulmus davidiana*, were prepared. Then, the nourishing lotion is tested for its skin-moisturizing and skin elasticity-enhancing effects. After the test, it is observed that the nourishing lotion shows markedly improved effects as compared to nourishing lotion not containing the above composition (see Tables 9 and 10).

In addition, the anti-aging composition disclosed herein may be used in such an amount that the user's skin is totally covered with the composition. There is no particular limitation in dose. Further, the anti-aging composition may be applied any time as desired by the user.

Hereinafter, additives that may be used in the composition disclosed herein will be explained in more detail.

There is no particular limitation in the additives that may be used herein, as long as the additives are generally known to those skilled in the art for use in formulating ointments or creams. Particular examples of such additives include oil and fat bases, such as Vaseline, liquid paraffin, paraffin, Plastibase, lard, vegetable oil, wax, purified lanolin, etc., aqueous bases, such as polyethylene glycol, etc., and emulsion bases, such as water-absorbing ointment, hydrophilic ointment, etc. To obtain formulations applicable to the composition disclosed herein, the additives may further include antioxidants, waterproofing agents, moisturizing agents, softening aids, or the like.

In another aspect, there is provided a cosmetic anti-aging composition including low-molecular weight hyaluronic acids, high-molecular weight hyaluronic acids and polysaccharides extracted from root bark of Ulmus davidiana, as active ingredients.

The cosmetic anti-aging composition disclosed herein has moisturizing, skin elasticity-enhancing and anti-inflammatory effects.

The cosmetic anti-aging composition disclosed herein is shown to have anti-aging activities in itself. Therefore, the anti-aging composition may be formed into any formulations applied onto the skin or hair. Particular examples of such formulations include skin lotions, skin softeners, skin toners, astringents, lotions, milk lotions, moisturizing lotions, nourishing lotions, massage creams, nourishing creams, moisturizing creams, hand creams, foundations, essences, nourishing essences, packs, soap, cleansing foam, cleansing lotions, cleansing creams, body lotions and body cleansers.

MODE FOR INVENTION

The examples and experiments will now be described. The following examples and experiments are for illustrative purposes only and not intended to limit the scope of the present invention.

Example 1

Preparation of Compositions of Hyaluronic Acids and Polysaccharides from Root Bark of Ulmus Davidiana with Different Ratios and Test for Measuring Their Effects First, high-molecular weight hyaluronic acids (average M.W.: 500,000-3,000,000 Da, prepared by the method of Korean Patent Publication No. 1989-0003708), low-molecular weight hyaluronic acids (average M.W.: 500-10,000 Da, prepared by the method of Korean Patent Registration No. 10-0665916-0000) and polysaccharides from root bark of Ulmus davidiana (prepared by the method of Korean Patent Registration No. 10-0445430-0000) are mixed in the ratios as set forth in Table 1 (wt % basis). Then, the resultant mixture is dissolved in purified water to a solid content of 1 g/L (final concentration of 0.1%).

TABLE 1

| | Compositional Ratio (%) | | |
|---|---|---|---|
| | Low-M.W. Hyaluronic acid | High-M.W. Hyaluronic acid | Polysaccharides of Ulmus macrocarpa Hance |
| Example 1-1 | 33.3 | 33.3 | 33.3 |
| Example 1-2 | 50 | 25 | 25 |
| Example 1-3 | 60 | 20 | 20 |
| Example 1-4 | 66.7 | 16.7 | 16.7 |
| Example 1-5 | 25 | 50 | 25 |
| Example 1-6 | 20 | 60 | 20 |
| Example 1-7 | 16.6 | 66.6 | 16.6 |
| Example 1-8 | 25 | 25 | 50 |
| Example 1-9 | 20 | 20 | 60 |
| Example 1-10 | 16.7 | 16.7 | 66.7 |
| Example 1-11 | 40 | 40 | 20 |
| Example 1-12 | 20 | 40 | 40 |
| Example 1-13 | 40 | 20 | 40 |
| Comp. Ex. 1 | 100 | 0 | 0 |
| Comp. Ex. 2 | 0 | 100 | 0 |
| Comp. Ex. 3 | 0 | 0 | 100 |

Test Example 1

Measurement of Moisturizing Effect (Corneometer 825)

Each composition prepared with the ratios as set forth in Table 1 is tested for measuring the moisturizing effect. Twenty male and female subjects (five male subjects and fifteen female subjects) aged 22-33 participated in the test. Each individual subject had no skin diseases that may affect the test results. Before the samples are applied to each subject, the test portions are cleaned with water and accommodated to the external environment for 30 minutes. The test is carried out under the same conditions (ambient temperature of 22-24° C. and humidity of 45-50%). Next, 10 μL of each sample is applied to the inner side of the upper arm of each subject to 2×2 cm², followed by drying for one minute. Then, 20 μL of purified water is further applied to each treated portion, and excessive water is wiped off by using KimWipes. Immediately thereafter, the electrostatic capacity at each treated portion on the skin surface is measured by using Corneometer CM 825 (Courage and Khazaka, Köln, Germany) at an interval of one minute (at 0, 1, 2, 3, 4, 5, 6, 7, 8 and 9 minutes). The moisturizing effect is determined by using Equation 1, and the results are shown in Table 2. The listed values are expressed in Corneometer value (Cv) unit.

Improvement in moisturization(%)={[(Measurement at each time)−(Measurement at the baseline)]/(Measurement at the baseline)}×100    [Equation 1]

TABLE 2

| | Time (min) | | | | | |
|---|---|---|---|---|---|---|
| Sample | 0 | 2 | 4 | 6 | 8 | 10 |
| Example 1-1 | 164.3 | 75.79 | 62.3 | 56.0 | 53.4 | 48.4 |
| Example 1-2 | 163.5 | 71.2 | 65.5 | 54.0 | 50.6 | 48.4 |
| Example 1-3 | 168.2 | 75.4 | 67.1 | 58.1 | 56.7 | 58.6 |
| Example 1-4 | 182.6 | 87.1 | 72.3 | 65.9 | 62.1 | 61.4 |
| Example 1-5 | 154.3 | 69.0 | 62.2 | 53.6 | 51.3 | 45.0 |
| Example 1-6 | 156.0 | 70.2 | 65.1 | 53.4 | 51.8 | 51.0 |
| Example 1-7 | 152.8 | 69.4 | 64.5 | 50.3 | 52.3 | 46.0 |
| Example 1-8 | 163.2 | 73.5 | 69.0 | 51.3 | 51.7 | 49.7 |
| Example 1-9 | 167.5 | 76.0 | 68.2 | 57.5 | 53.4 | 52.6 |
| Example 1-10 | 169.5 | 78.1 | 66.5 | 53.7 | 52.3 | 49.5 |
| Example 1-11 | 172.3 | 82.1 | 69.2 | 54.0 | 52.8 | 53.4 |

TABLE 2-continued

| Sample | Time (min) | | | | | |
|---|---|---|---|---|---|---|
| | 0 | 2 | 4 | 6 | 8 | 10 |
| Example 1-12 | 174.1 | 81.1 | 68.4 | 55.0 | 49.6 | 50.3 |
| Example 1-13 | 166.4 | 75.1 | 68.2 | 55.1 | 51.6 | 49.6 |
| Comp. Ex. 1 | 157.3 | 75.79 | 62.35 | 52.43 | 47.79 | 44.5 |
| Comp. Ex. 2 | 164 | 70.1 | 60.2 | 53.73 | 51.88 | 46.3 |
| Comp. Ex. 3 | 160.2 | 73.5 | 61.2 | 54.3 | 50.9 | 43.2 |

After the test, it is observed that the composition including the low-molecular weight hyaluronic acids, high-molecular weight hyaluronic acids and polysaccharides extracted from root bark of *Ulmus davidiana* as active ingredients shows an improved moisturizing effect, as compared to a composition including low-molecular weight hyaluronic acids, high-molecular weight hyaluronic acids or polysaccharides extracted from root bark of *Ulmus davidiana* alone.

Test Example 2

Test for Measuring Skin Elasticity-Enhancing Effect

An elasticity measuring system, Cutometer MPA580 (Courage and Khazaka, Köln, Germany), is used to measure the skin elasticity in terms of R5 values. The system is based on the principle that when a negative pressure is continuously applied to the skin for a predetermined time to cause the skin to be sucked into a probe, and then the negative pressure is removed, the skin returns to its original shape. The probe with a diameter of 2 mm connected to the system is allowed to be in close contact with the shaved skin and the skin elasticity is measured in a noninvasive manner. The skin elasticity is measured before each sample is applied to the skin. Then, 25 mL/cm² of each sample is applied to the upper arm. The skin elasticity is measured one hour after the application. The test is carried out in a constant-temperature, constant-humidity room maintained at a temperature of 20° C. and a humidity of 50%. Twenty male and female subjects in their 20s and 30s participated in the test. The skin elasticity-enhancing effect is determined by using Equation 2, and the results are shown in Table 3.

Improvement in skin elasticity(%)={[($R5$ measurement for each sample)−(Initial $R5$ measurement)]/(Initial $R5$ measurement)}×100  [Equation 2]

TABLE 3

| Sample | Improvement in Skin Elasticity (%) |
|---|---|
| Example 1-1 | 13.8 |
| Example 1-2 | 13.0 |
| Example 1-3 | 26.8 |
| Example 1-4 | 34.1 |
| Example 1-5 | 22.4 |
| Example 1-6 | 16.4 |
| Example 1-7 | 19.7 |
| Example 1-8 | 13.6 |
| Example 1-9 | 14.0 |
| Example 1-10 | 15.8 |
| Example 1-11 | 27.0 |
| Example 1-12 | 22.2 |
| Example 1-13 | 24.3 |
| Comp. Ex. 1 | 5.4 |
| Comp. Ex. 2 | 4.9 |
| Comp. Ex. 3 | 2.1 |

After the test, it is observed that the composition including the low-molecular weight hyaluronic acids, high-molecular weight hyaluronic acids and polysaccharides extracted from root bark of *Ulmus davidiana* as active ingredients shows an unexpectedly markedly improved skin elasticity-enhancing effect, as compared to a composition including low-molecular weight hyaluronic acids, high-molecular weight hyaluronic acids or polysaccharides extracted from root bark of *Ulmus davidiana* alone.

Test Example 3

Measurement of Anti-Inflammatory Effect
(Measurement of Effect of Inhibiting Expression of iNOS and COX-2 Genes)

Mouse macrophages, Raw264.7 cells (ATCC TIB-71), are treated with lipopolysaccharide to artificially increase expression of cyclooxygenase 2 (COX 2) genes. Next, effects of samples (Examples 1-1 to 1-14 and Comparative Examples) on the inhibition of the gene expression are measured by using the reverse transcription-polymerase chain reaction (RT-PCR) method (see, Green L. et al., *Anal. Biochem.*, 126, pp. 131-138, 1982). In 10% FBS-DMEM medium, $8 \times 10^5$ cells are suspended. Then, the cell suspension is inoculated and adhered to a 100 mm dish. After one day, the cells are treated with 25 μg/mL of each sample (Examples 1-1 to 1-14 and Comparative Examples), incubated for 18 hours, treated with 1 μg/mL of lipopolysaccharide (LPS, available from Sigma Co.), and then further incubated for 8 hours. After that, the medium is removed from the cells, 1 mL of Trizol (Invitrogen Co.) is added thereto, and RNA is separated therefrom by the RNA separation method following Invitrogen's instructions. Then, RNA is quantitated at 260 nm and RT-PCR is carried out. To perform the RT-PCR, a commercially available All-in-One RT-PCR kit (Super-Bio Co.) is used in the presence of the primers under the conditions as set forth in Table 4.

TABLE 4

| iNOS Primer | Sense | 5'-CAGTTCTGCGCCTTTGCTCAT-3' (Seq. No. 1) |
|---|---|---|
| | antisense | 5'-GGTGGTGCGGCTGGACTTT-3' (Seq. No. 2) |
| | Reaction Condition | Reverse transcription is performed at 50° C. for 30 min, reverse transcriptase is deactivated at 96° C. for 3 min, and PCR is carried out with 32 cycles at 94° C. for 30 sec, at 60° C. for 30 sec and 72° C. for 1 min. |
| COX2 Primer | sense | 5'-CTGAAGCCCACCCCAAAC-3' (Seq. No. 3) |
| | antisense | 5'-AACCCAGGTCCTCGCTTATG-3' (Seq. No. 4) |
| | Reaction Condition | Reverse transcription is performed at 50° C. for 30 min, reverse transcriptase is deactivated at 96° C. for 3 min, and PCR is carried out with 32 cycles at 94° C. for 30 sec, at 55° C. for 30 sec and 72° C. for 1 min. |
| Actin Primer | sense | 5'-GAGACCTTCAACACCCCAGCC-3' (Seq. No. 5) |
| | antisense | 5'-GGCCATCTCTTGCTCGAAGTC-3' (Seq. No. 6) |
| | Reaction Condition | Reverse transcription is performed at 50° C. for 30 min, reverse transcriptase is deactivated at 96° C. for 3 min, and PCR is carried out with 32 cycles at 94° C. for 1 min, at 60° C. for 1 min and 72° C. for 1 min. |

The test is carried out according to the instruction manual provided with the All-in-One RT-PCR kit, and the results are shown in Table 5.

TABLE 5

| Sample | Inhibition of NOS Expression (%) | Inhibition of COX2 Expression (%) |
|---|---|---|
| Example 1-1 | 38.5 ± 2.9 | 26.0 ± 8.9 |
| Example 1-2 | 35.7 ± 7.0 | 37.9 ± 0.9 |
| Example 1-3 | 42.7 ± 6.0 | 57.0 ± 5.6 |
| Example 1-4 | 65.3 ± 5.7 | 67.3 ± 1.7 |
| Example 1-5 | 42.3 ± 4.0 | 46.6 ± 3.0 |
| Example 1-6 | 49.1 ± 3.2 | 30.4 ± 5.2 |
| Example 1-7 | 35.0 ± 9.2 | 31.5 ± 8.2 |
| Example 1-8 | 46.7 ± 8.6 | 45.9 ± 11.2 |
| Example 1-9 | 43.5 ± 3.6 | 38.9 ± 3.6 |
| Example 1-10 | 42.1 ± 3.9 | 38.2 ± 7.0 |
| Example 1-11 | 52.3 ± 7.2 | 56.8 ± 2.3 |
| Example 1-12 | 44.8 ± 4.0 | 35.8 ± 5.3 |
| Example 1-13 | 23.3 ± 4.8 | 30.1 ± 8.6 |
| Comp. Ex. 1 | 8.4 ± 3.3 | 14.0 ± 8.4 |
| Comp. Ex. 2 | 13.4 ± 6.3 | 16.5 ± 0.5 |
| Comp. Ex. 3 | 24.0 ± 5.0 | 38.5 ± 5.5 |

Preparation Example 1

Preparation of Skin Softener

Preparation of skin softener containing the composition according to Example 1-4 is shown in Table 6.

TABLE 6

| | | Amount (wt %) | |
|---|---|---|---|
| No. | Ingredients | Preparation Ex. 1 | Comp. Preparation Ex. 1 |
| 1 | Example 1-4 | 10.0 | — |
| 2 | Propylene glycol | 5.00 | 5.00 |
| 3 | Ethanol | 3.00 | 3.00 |
| 4 | Phenoxyethanol | 0.20 | 0.20 |
| 5 | Allantoin | 0.20 | 0.20 |
| 6 | Citric acid | 0.20 | 0.20 |
| 7 | Sodium citrate | 0.12 | 0.12 |
| 8 | Hydogenated castor oil | 0.10 | 0.10 |
| 9 | Methyl paraben | 0.10 | 0.10 |
| 10 | Combined flavor | 0.10 | 0.10 |
| 11 | Purified water | balance | Balance |

Formulation Example 1

Hydrogenated castor oil, methyl paraben and a combined flavor are dissolved into ethanol, and then the resultant solution is introduced and dissolved into purified water containing the remaining ingredients dissolved therein.

Comparative Formulation Example 1

Formulation Example 1 is repeated except that Ingredient 1 is not used.

Preparation Example 2

Preparation of Nourishing Lotion

Preparation of lotion containing the composition according to Example 1-4 is shown in Table 7.

TABLE 7

| | | Amount (wt %) | |
|---|---|---|---|
| No. | Ingredients | Preparation Ex. 2 | Comp. Preparation Ex. 2 |
| 1 | Example 1-4 | 10.0 | — |
| 2 | Stearic acid | 0.4 | 0.4 |
| 3 | 1,3-Butylene glycol | 6.0 | 6.0 |
| 4 | Cetostearyl alcohol | 1.2 | 1.2 |
| 5 | Glycerin | 4.0 | 4.0 |
| 6 | Glyceryl stearate sorbitan stearate | 1.0 | 1.0 |
| 7 | Triethanol amine | 0.2 | 0.2 |
| 8 | Tocopheryl acetate | 3.0 | 3.0 |
| 9 | Liquid paraffin | 5.0 | 5.0 |
| 10 | Squalane | 3.0 | 3.0 |
| 11 | Macadamia nut oil | 2.0 | 2.0 |
| 12 | Polysorbate 60 | 1.5 | 1.5 |
| 13 | Sorbitan sesquioleate | 0.5 | 0.5 |
| 14 | Caboxyvinyl polymer | 0.10 | 0.10 |
| 15 | Methyl paraben | 0.10 | 0.10 |
| 16 | Combined Flavor | 0.10 | 0.10 |
| 17 | Purified water | balance | Balance |

Formulation Example 2

The above-described ingredients are subjected to an emulsification process, wherein the oil-soluble ingredients serve as an oil phase and the ingredients soluble in purified water serve as an aqueous phase, by homogeneously mixing the oil phase and the aqueous phase in a homogenizer at a constant temperature (80-85° C.). Next, a thickener (Carbomer) is neutralized and cooled, Ingredient 1 is added thereto, and the resultant mixture is degassed to obtain a formulation.

Comparative Formulation Example 2

Formulation Example 2 is repeated, except that Ingredient 1 is not used.

Preparation Example 3

Preparation of Nourishing Cream

Preparation of nourishing cream containing the composition according to Example 1-4 is shown in Table 8.

TABLE 8

| | | Amount (wt %) | |
|---|---|---|---|
| No. | Ingredients | Preparation Ex. 3 | Comp. Preparation Ex. 3 |
| 1 | Example 1-4 | 10.0 | — |
| 2 | Glycerin | 6.00 | 6.00 |
| 3 | Squalane | 6.00 | 6.00 |
| 4 | Isohexadecane | 5.50 | 5.50 |
| 5 | Cetyl octanoate | 4.00 | 4.00 |
| 6 | Glyceryl stearate | 2.50 | 2.50 |
| 7 | Polysorbate 60 | 1.00 | 1.00 |
| 8 | PEG-100 stearate | 1.00 | 1.00 |
| 9 | Stearic acid | 1.00 | 1.00 |
| 10 | Lanolin | 1.00 | 1.00 |
| 11 | Laureth-12 | 1.00 | 1.00 |
| 12 | Cetyl alcohol | 0.50 | 0.50 |
| 13 | Sorbitan sesquioleate | 0.30 | 0.30 |
| 14 | Carbomer | 0.30 | 0.30 |
| 15 | Triethanol amine | 0.30 | 0.30 |
| 16 | Methyl paraben | 0.20 | 0.20 |
| 17 | Imidazolinyl urea | 0.15 | 0.15 |
| 18 | Propyl paraben | 0.10 | 0.10 |

TABLE 8-continued

| | | Amount (wt %) | |
|---|---|---|---|
| No. | Ingredients | Preparation Ex. 3 | Comp. Preparation Ex. 3 |
| 19 | Combined Flavor | 0.10 | 0.10 |
| 20 | Purified water | balance | Balance |

Formulation Example 3

The above-described ingredients are subjected to an emulsification process, wherein the oil-soluble ingredients serve as an oil phase and the ingredients soluble in purified water serve as an aqueous phase, by homogeneously mixing the oil phase and the aqueous phase in a homogenizer at a constant temperature (80-85° C.). Next, a thickener (Carbomer) is neutralized and cooled, Ingredient 1 is added thereto, and the resultant mixture is degassed to obtain a formulation.

Comparative Formulation Example 3

Formulation Example 3 is repeated, except that Ingredient 1 is not used.

Preparation Example 4

Preparation of Hydrophilic Ointment

TABLE 9

| | | Amount (wt %) | |
|---|---|---|---|
| No. | Ingredients | Preparation Ex. 4 | Comp. Preparation Ex. 4 |
| 1 | Example 1-4 | 10 | — |
| 2 | White Vaseline | 25 | 25 |
| 3 | Stearyl alcohol | 22 | 22 |
| 4 | Ethyl (or Methyl) p-oxybenzoate | 0.25 | 0.25 |
| 5 | Propylene glycol | 12 | 12 |
| 6 | Sodium lauryl sulfate | 15 | 15 |
| 7 | Propyl p-oxybenzoate | 0.15 | 0.15 |
| 8 | Purified water | balance | Balance |

Formulation Example 4

The above-described ingredients are subjected to an emulsification process, wherein the oil-soluble ingredients serve as an oil phase and the ingredients soluble in purified water serve as an aqueous phase, by homogeneously mixing the oil phase and the aqueous phase in a homogenizer at a constant temperature (80-85° C.). Next, a thickener (Carbomer) is neutralized and cooled, Ingredient 1 is added thereto, and the resultant mixture is degassed to obtain a formulation.

Comparative Formulation Example 4

Formulation Example 4 is repeated, except that Ingredient 1 is not used.

Clinical Test Example 1

Test for Measuring Skin-Moisturizing Effect

This test is carried out for twelve subjects. For the test, the subjects are asked to take a shower in the morning without using any soap or cleanser and to visit the Ellead Skin Research Center. Then, they are asked to wash their left and right front arms from the wrist to the elbow only with flowing water. The test portion of the front arm is from the bent portion spaced apart from the wrist by a distance of 5 cm. Six squares with a side length of 2 cm are drawn at an interval of 1.5 cm on the test portion. Three test portions are randomly selected from each of the right front arm and the left front arm.

The test portions are kept under a constant-temperature constant-humidity condition for 30 minutes. After that, the test portions are examined five times by using the Corneometer CM825 (Courage & Khazaka, Germany). Three measurements except the highest and the lowest values are averaged (baseline).

The samples of Formulation Example 2 and Comparative Example 2 are applied to the test portions, each in an amount of 5 μL/cm². Then, purified water is further applied thereto, 9.5 minutes after the application. Thirty seconds after the application of purified water, water is removed by using Kim-Wipes. After that, the test portions are examined again five times at an interval of one minute (0, 1, 2, 3, 4, 5, 6, 7 and 8 minutes) by using the Corneometer (CM825, Courage & Khazaka, Germany). Three measurements except the highest and the lowest values are averaged.

The measurements of the Corneometer before the application of the samples (baseline, 0 min.), and after the lapse of 1, 2, 3, 4, 5, 6, 7 and 8 minutes are used to calculate the difference between the measurement at each time and the measurement before the application of the samples. In this manner, an improvement in skin moisturization (%) is obtained by calculating the percentage of the difference at each time based on the measurement before the application of the samples. The results are shown in Table 10.

TABLE 10

| Improvement (%) | Comp. Formulation Ex. 2 | Formulation Ex. 2 |
|---|---|---|
| 0 min | 174.18 | 174.08 |
| 1 min | 95.89 | 110.14 |
| 2 min | 84.53 | 90.23 |
| 3 min | 66.41 | 74.44 |
| 4 min | 62.35 | 80.25 |
| 5 min | 70.16 | 81.87 |
| 6 min | 68.33 | 80.74 |
| 7 min | 63.33 | 78.18 |
| 8 min | 61.12 | 79.54 |

As can be seen from Table 10, the lotion of Formulation Example 2 using the composition disclosed herein that includes low-molecular weight hyaluronic acids, high-molecular weight hyaluronic acids and extract of root bark of *Ulmus davidiana* has a significantly improved skin-moisturizing effect, as compared to the lotion of Comparative Formulation Example 2.

Clinical Test Example 2

Test for Measuring Skin Elasticity-Improving Effect

To determine the effect of the composition disclosed herein upon skin wrinkles, the lotions according to Formulation Example 2 and Comparative Formulation Example 2 are applied to twenty female subjects aged 20-55. The subjects had normal type, oily type, dry type and mixed type skin. The lotion of Formulation Example 2 and the lotion of Comparative Formulation Example 2 are applied to the left side of and the right side of the face of each subject, respectively, twice a day, in the morning and at night. After two weeks and four weeks, the skin elasticity of each subject is determined by using a skin elasticity tester (Ballistometer). The results are shown in Table 11.

TABLE 11

| | | | Cosmetic agent of Formulation Ex. 2 | | | Cosmetic agent of Comp. Formulation Ex. 2 | | |
|---|---|---|---|---|---|---|---|---|
| | | | $T_0$ | $T_2$ | $T_4$ | $T_0$ | $T_2$ | $T_4$ |
| Skin Elasticity | Bounce | | 0.0 | 0.0 | 0.0 | 0.0 | 0.0 | 0.0 |
| | AMPLITUDE | First | 1.9 | 3.2 | 3.5 | 1.9 | 2.8 | 2.7 |
| | | Second | 1.1 | 2.2 | 3.3 | 1.3 | 2.0 | 2.1 |
| | | Third | 0.0 | 1.6 | 1.7 | 0.0 | 0.9 | 1.5 |
| | | Fourth | 0.0 | 0.4 | 0.9 | 0.0 | 0.0 | 0.0 |
| | Average | | 0.75 | 1.85 | 2.35 | 0.80 | 1.425 | 1.575 |
| | Remark | | $T_0$: Before use, $T_2$: 2 weeks after use, $T_4$: 4 weeks after use | | | | | |

As can be seen from Table 11, the lotion of Formulation Example 2 using the composition disclosed herein that includes low-molecular weight hyaluronic acids, high-molecular weight hyaluronic acidsand extract of root bark of *Ulmus davidiana* has a significantly improved skin elasticity-enhancing effect, as compared to the lotion of Comparative Formulation Example 2.

INDUSTRIAL APPLICABILITY

As can be seen from the foregoing, the composition including the low-molecular weight hyaluronic acids (average M.W.: 500-50,000 Da), high-molecular weight hyaluronic acids (average M.W.: 500,000-3,000,000 Da) and polysaccharides extracted from root bark of *Ulmus davidiana*, in a predetermined ratio, shows significantly improved skin-moisturizing, skin elasticity-enhancing and inflammation-alleviating effects, as compared to a composition using one of the above ingredients alone. When measuring the skin moisturizing effect of the composition disclosed herein with the Corneometer 825, the composition shows an improved skin-moisturizing effect, as compared to the composition using one of the above ingredients alone. In addition, the results of the skin elasticity test and anti-inflammation test reveal that the composition disclosed herein shows improved skin elasticity-enhancing and anti-inflammatory effects. Therefore, the composition may be widely used as a pharmaceutical or cosmetic anti-aging composition.

While the exemplary embodiments have been shown and described, it will be understood by those skilled in the art that various changes in form and details may be made thereto without departing from the spirit and scope of the present invention as defined by the appended claims.

In addition, many modifications can be made to adapt a particular situation or material to the teachings of the present invention without departing from the essential scope thereof. Therefore, it is intended that the present invention not be limited to the particular exemplary embodiments disclosed as the best mode contemplated for carrying out the present invention, but that the present invention will include all embodiments falling within the scope of the appended claims.

The invention claimed is:

1. A composition for external use on skin, which comprises 15 to 70 wt. % of low-molecular weight hyaluronic acids, 15 to 60 wt % of high-molecular weight hyaluronic acids, and 15 to 60 wt % of polysaccharides extracted from root bark of *Ulmus davidiana*, as active ingredients, wherein the weight is based on the total weight of the composition, wherein the high-molecular weight hyaluronic acids have an average molecular weight of 500,000 Da to 3,000,000 Da, and the low-molecular weight hyaluronic acids have an average molecular weight of 500 Da to 50,00 Da, and wherein skin treated with the composition demonstrates an increased skin elasticity-enhancing effect as compared to skin treated with a composition including only one of low-molecular weight hyaluronic acids, high-molecular weight hyaluronic acids, or polysaccharides extracted from root bark of *Ulmus davidiana*.

2. The composition for external use on skin according to claim 1, which has moisturizing, skin elasticity-enhancing and anti-inflammatory effects.

3. The composition for external use on skin according to claim 1, which is provided in any one formulation selected from the group consisting of cream, gel, patch, spray agent, ointment, plaster, lotion, liniment, paste and cataplasm.

4. The composition for external use on skin according to claim 1, which is provided in any one formulation selected from the group consisting of skin lotion, skin softener, skin toner, astringent, lotion, milk lotion, moisturizing lotion, nourishing lotion, massage cream, nourishing cream, moisturizing cream, hand cream, foundation, essence, nourishing essence, pack, soap, cleansing foam, cleansing lotion, cleansing cream, body lotion and body cleanser.

* * * * *

SEQUENCE LISTING

```
<160> NUMBER OF SEQ ID NOS: 6

<210> SEQ ID NO 1
<211> LENGTH: 21
<212> TYPE: DNA
<213> ORGANISM: Artificial Sequence
<220> FEATURE:
<223> OTHER INFORMATION: sense primer for PCR of iNOS

<400> SEQUENCE: 1
cagttctgcg cctttgctca t                                      21

<210> SEQ ID NO 2
<211> LENGTH: 19
<212> TYPE: DNA
<213> ORGANISM: Artificial Sequence
<220> FEATURE:
<223> OTHER INFORMATION: antisense primer for PCR of iNOS

<400> SEQUENCE: 2
ggtggtgcgg ctggacttt                                         19

<210> SEQ ID NO 3
<211> LENGTH: 18
<212> TYPE: DNA
<213> ORGANISM: Artificial Sequence
<220> FEATURE:
<223> OTHER INFORMATION: sense primer for PCR of COX2
```

```
<400> SEQUENCE: 3
ctgaagccca ccccaaac                                                  18

<210> SEQ ID NO 4
<211> LENGTH: 20
<212> TYPE: DNA
<213> ORGANISM: Artificial Sequence
<220> FEATURE:
<223> OTHER INFORMATION: antisense primer for PCR of COX2

<400> SEQUENCE: 4
aacccaggtc ctcgcttatg                                                20

<210> SEQ ID NO 5
<211> LENGTH: 21
<212> TYPE: DNA
<213> ORGANISM: Artificial Sequence
<220> FEATURE:
<223> OTHER INFORMATION: sense primer for PCR of Actin

<400> SEQUENCE: 5
gagaccttca acaccccagc c                                              21

<210> SEQ ID NO 6
<211> LENGTH: 21
<212> TYPE: DNA
<213> ORGANISM: Artificial Sequence
<220> FEATURE:
<223> OTHER INFORMATION: antisense primer for PCR of Actin

<400> SEQUENCE: 6
ggccatctct tgctcgaagt c                                              21
```